(12) United States Patent
Varela, III

(10) Patent No.: US 8,112,828 B1
(45) Date of Patent: Feb. 14, 2012

(54) TOILET ANTI-SPLATTER APPARATUS

(76) Inventor: Manuel B. Varela, III, Auburn, CA (US)

( * ) Notice: Subject to any disclaimer, the term of this patent is extended or adjusted under 35 U.S.C. 154(b) by 420 days.

(21) Appl. No.: 12/490,057

(22) Filed: Jun. 23, 2009

(51) Int. Cl.
*E03D 9/00* (2006.01)
(52) U.S. Cl. .............................. 4/300.3; 4/661
(58) Field of Classification Search ............ 4/300.3, 4/661, DIG. 5, 902
See application file for complete search history.

(56) References Cited

U.S. PATENT DOCUMENTS

| | | | |
|---|---|---|---|
| 3,383,710 A * | 5/1968 | Carmichael | 4/300.3 |
| 4,044,405 A | 8/1977 | Kreiss | |
| 4,744,113 A * | 5/1988 | Kogut | 4/661 |
| 5,031,253 A | 7/1991 | Brendlinger | |
| 5,117,515 A | 6/1992 | White, Jr. et al. | |
| D402,016 S | 12/1998 | Walton | |
| 6,183,850 B1 | 2/2001 | Lauer | |
| 6,908,392 B2 | 6/2005 | Friedman et al. | |
| 7,373,673 B1 | 5/2008 | Holland | |
| 7,393,673 B2 * | 7/2008 | Adney et al. | 435/209 |
| 2006/0179563 A1 | 8/2006 | Kneese et al. | |
| 2007/0039096 A1 * | 2/2007 | Smitherman | 4/661 |

* cited by examiner

*Primary Examiner* — Gregory Huson
*Assistant Examiner* — Karen L Younkins

(57) ABSTRACT

The toilet anti-splatter apparatus limits urine splash in a toilet. The apparatus is provided in a plurality of sheets, all combined in a stack with one edge having a releasable bond. Each sheet provides a floating target with bulls eye containing a foaming agent. Upon water contact, the surfactant foaming agent foams, thereby diminishing splatter. The sheets are disposable and biodegradable and further inhibit splatter by floating until flushed. Available embodiments of the apparatus include those with bactericidal and fungicidal chemicals within the center capsule. Further embodiments contains dyes to encourage target strike by the user.

11 Claims, 3 Drawing Sheets

TOILET ANTI-SPLATTER APPARATUS

BACKGROUND OF THE INVENTION

A host of devices have been proposed to prevent male urine splatter in a toilet bowl. Some simply have not worked. Others are avoided by toilet users. Many must remain in the toilet, an obvious shortcoming due at least in part to means that must be used to retain them there. Some are designed to be flushed after use, but do not flush easily in many toilets and can therefore clog the toilet. Some are too expensive to be cost effective. The present apparatus solves these problems and more in providing a flushable, biodegradable target that is effective in limiting urine splatter, is cost effective, and encourages use.

FIELD OF THE INVENTION

The toilet anti-splatter apparatus relates to toilet targets and more especially to a toilet anti-splatter apparatus that helps prevent male urine splatter.

SUMMARY OF THE INVENTION

The general purpose of the toilet anti-splatter apparatus, described subsequently in greater detail, is to provide a toilet anti-splatter apparatus which has many novel features that result in an improved toilet anti-splatter apparatus which is not anticipated, rendered obvious, suggested, or even implied by prior art, either alone or in combination thereof.

To attain this, the toilet anti-splatter apparatus limits urine splash in a toilet. The apparatus floats until the toilet is flushed. Flotation is enhanced by the foaming action of the foaming agent within the bulls eye. The apparatus is provided in a plurality of sheets, all combined in a stack with one edge having a releasable bond, much like paper sheets that pull off of a tablet. Each sheet provides a target with bulls eye and center bulls eye. When the apparatus is placed in the toilet bowl, an immediate reaction to water causes foaming from the foaming agent. The foaming agent is a surfactant which comprises a gas releasing compound. The foaming agent is available in various chemical makeups that include but are not limited to sodium bicarbonate, sodium lauryl sulfate, and ammonium lauryl sulfate. Various dies are also used to caused colorized foaming. By providing the sheets in a tablet, production cost is minimal which is reflected in low sales price. Use of the apparatus is thereby further encouraged due to cost effectiveness. The sheets are disposable and biodegradable. Available embodiments of the apparatus include those with bactericidal and fungicidal chemicals within the center capsule.

Thus has been broadly outlined the more important features of the improved toilet anti-splatter apparatus so that the detailed description thereof that follows may be better understood and in order that the present contribution to the art may be better appreciated.

An object of the toilet anti-splatter apparatus is to prevent urine splash in a toilet.

A further object of the toilet anti-splatter apparatus is to initiate foaming immediately upon contact with water.

An object of the toilet anti-splatter apparatus is to float until flushed.

Another object of the toilet anti-splatter apparatus is to be disposable.

An added object of the toilet anti-splatter apparatus is to be biodegradable.

And, an object of the toilet anti-splatter apparatus is to provide a target for men to aid in eliminating most urine splatter.

Yet another object of the toilet anti-splatter apparatus is to be cost effective.

Still another object of the toilet anti-splatter apparatus is to provide a bactericide.

And, a further object of the toilet anti-splatter apparatus is to provide a fungicide.

These together with additional objects, features and advantages of the improved toilet anti-splatter apparatus will be readily apparent to those of ordinary skill in the art upon reading the following detailed description of presently preferred, but nonetheless illustrative, embodiments of the improved toilet anti-splatter apparatus when taken in conjunction with the accompanying drawings.

In this respect, before explaining the current embodiments of the improved toilet anti-splatter apparatus in detail, it is to be understood that the toilet anti-splatter apparatus is not limited in its application to the details of construction and arrangements of the components set forth in the following description or illustration. Those skilled in the art will appreciate that the concept of this disclosure may be readily utilized as a basis for the design of other structures, methods, and systems for carrying out the several purposes of the improved toilet anti-splatter apparatus. It is therefore important that the claims be regarded as including such equivalent constructions insofar as they do not depart from the spirit and scope of the toilet anti-splatter apparatus. It is also to be understood that the phraseology and terminology employed herein are for purposes of description and should not be regarded as limiting.

DETAILED DESCRIPTION OF THE DRAWINGS

With reference now to the drawings, and in particular FIGS. 1 through 5 thereof, the principles and concepts of the toilet anti-splatter apparatus generally designated by the reference number 10 will be described.

Figure 1:
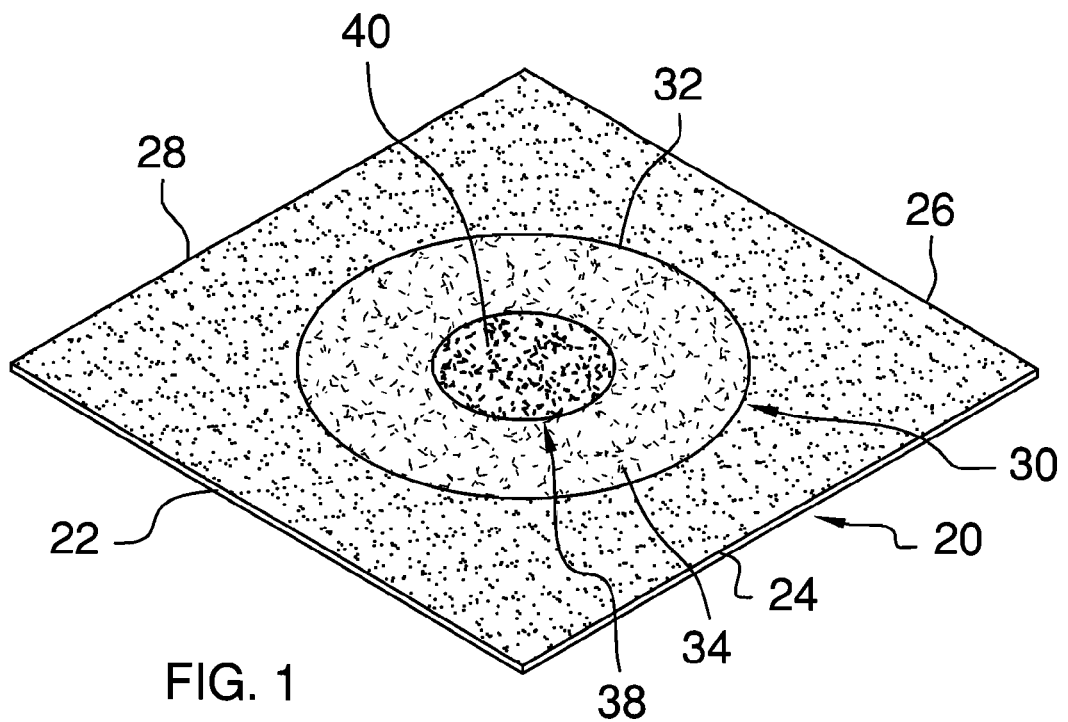
FIG. 1 is a perspective view of a single sheet of the apparatus.
Figure 2:
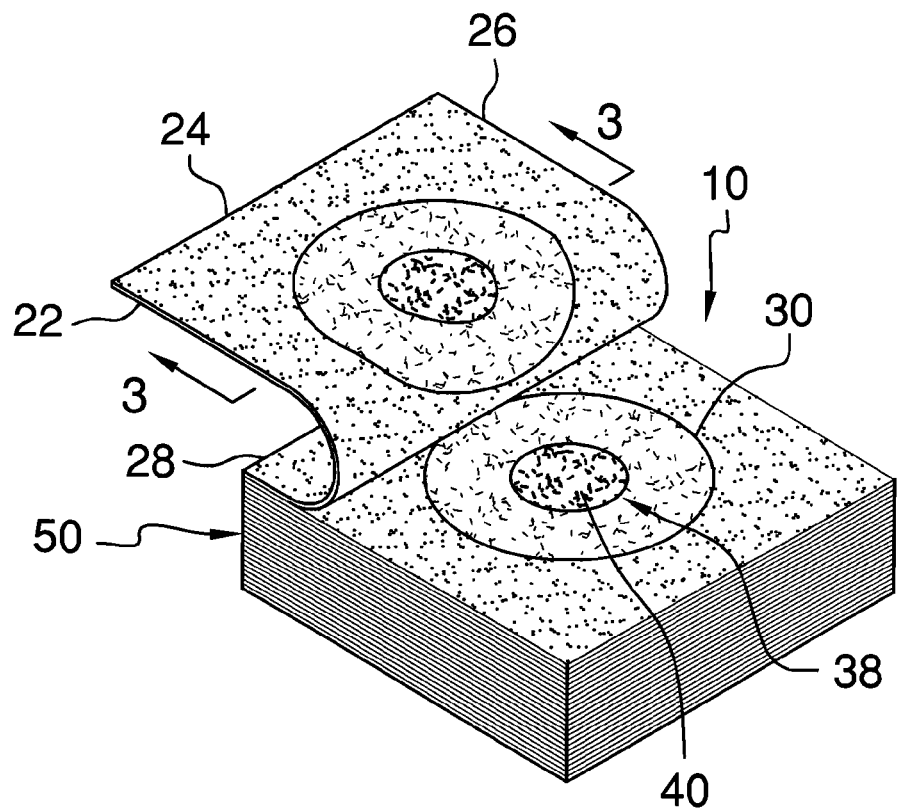
FIG. 2 is a perspective view of the apparatus, one unit peeled upwardly.
Figure 3:
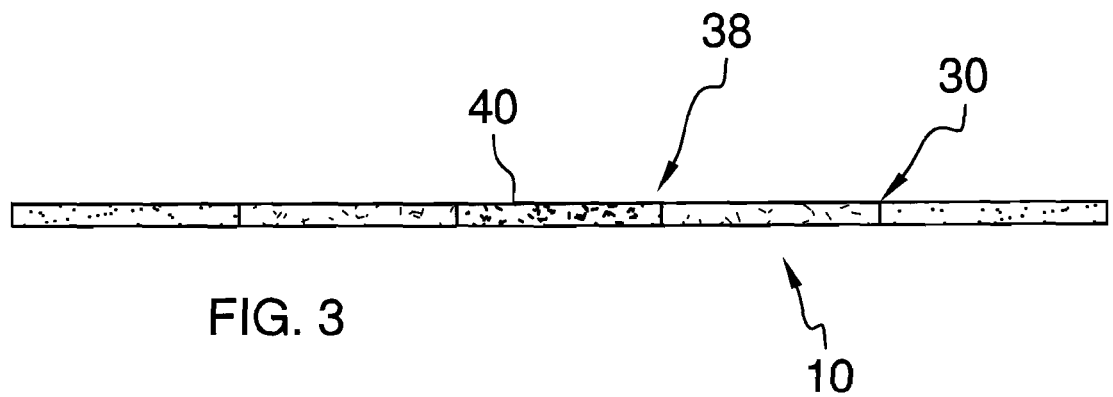
FIG. 3 is a cross sectional view of FIG. 2, taken along the line 3-3.

Referring to FIGS. 1 and 2, the apparatus 10 comprises a plurality of square single sheets 20 stacked one atop the next. Each sheet 20 has a first side 22 spaced apart from a third side 26 and a second side 24 spaced apart from a fourth side 28. The releasable bond 50 secures the fourth side 28 of all sheets 20.

Referring to FIG. 3 and again to FIG. 1, the circular border 32 defines an interior 34 of each sheet 20. The circular border 32 defines the bulls eye 30. The smaller circular center bulls eye 38 is disposed within the bulls eye 30.

Figure 4:
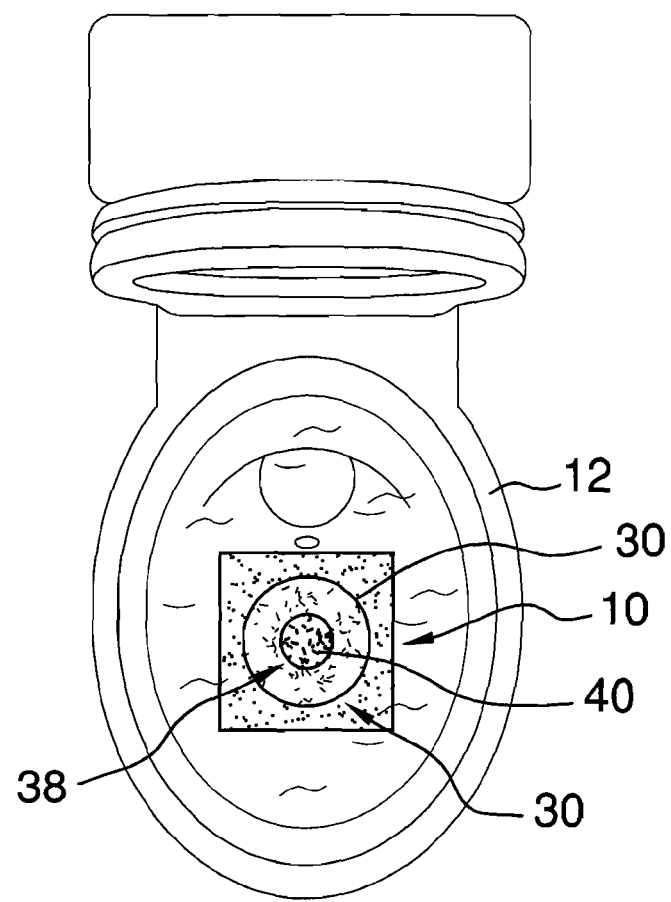
FIG. 4 is a top plan vie of one sheet in use
Figure 5:
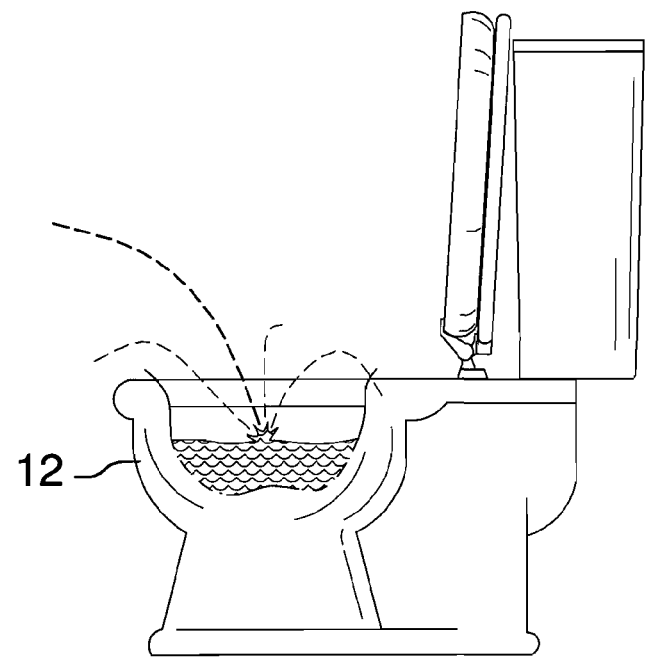
FIG. 5 is a pair of lateral elevation views, exemplifying the effects of urination with and without the apparatus.
Figure 5:
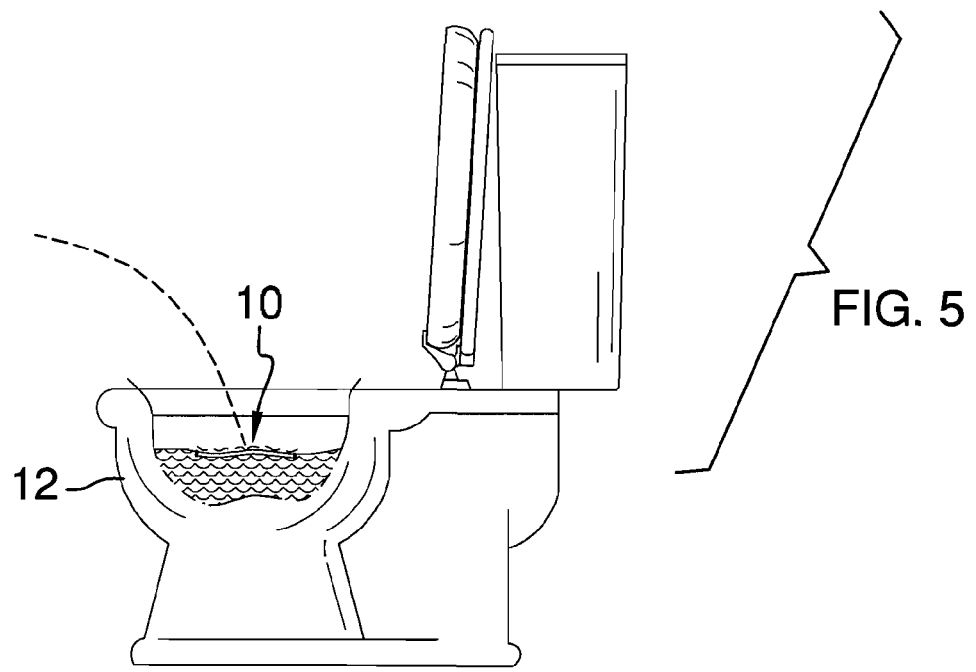

Referring to FIGS. 4 and 5, the foaming agent capsule 40 within the bulls eye 30 begins foaming immediately upon water contact. The capsule 40 thereby releases the foaming agent within. The foam is contacted by the urine stream and inhibits urine splatter.

Referring to FIG. 5 topmost illustration, the absence of the apparatus 10 exemplifies typical urine splatter present in a toilet bowl 12. The lowermost, comparative illustration exemplifies the function of the floating apparatus 10.

The apparatus, as claimed, provides the unexpected benefit of enhanced flotation due to the chemical foaming. The combination of such claimed elements provides this unpredictable and unexpected result that is not rendered obvious to one skilled in the art.

With respect to the above description then, it is to be realized that the optimum dimensional relationships for the parts of the toilet anti-splatter apparatus, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the toilet anti-splatter apparatus.

Directional terms such as "front", "back", "in", "out", "downward", "upper", "lower", and the like may have been used in the description. These terms are applicable to the embodiments shown and described in conjunction with the drawings. These terms are merely used for the purpose of description in connection with the drawings and do not necessarily apply to the position in which the toilet anti-splatter apparatus may be used.

Therefore, the foregoing is considered as illustrative only of the principles of the toilet anti-splatter apparatus. Further, since numerous modifications and changes will readily occur to those skilled in the art, it is not desired to limit the toilet anti-splatter apparatus to the exact construction and operation shown and described, and accordingly, all suitable modifications and equivalents may be resorted to, falling within the scope of the toilet anti-splatter apparatus.

What is claimed is:

1. A toilet anti-splatter apparatus, comprising:
a plurality of square single sheets stacked one atop the next, each sheet having a first side spaced apart from a third side, a second side spaced apart from a fourth side;
a releasable bond securing the fourth side of all sheets;
an interior circular border defining a interior of each sheet designated as a bulls eye;
a smaller circular center bulls eye within the bulls eye;
a foaming agent capsule within the bulls eye, whereby the capsule releases the foaming agent upon water contact.

2. The apparatus according to claim 1 wherein the apparatus is further biodegradable.

3. The apparatus according to claim 1 wherein the foaming agent is further bactericidal.

4. The apparatus according to claim 2 wherein the foaming agent is further bactericidal.

5. The apparatus according to claim 1 wherein the foaming agent is further fungicidal.

6. The apparatus according to claim 2 wherein the foaming agent is further fungicidal.

7. The apparatus according to claim 3 wherein the foaming agent is further fungicidal.

8. The apparatus according to claim 4 wherein the foaming agent is further fungicidal.

9. A toilet anti-splatter apparatus, comprising:
a plurality of square single sheets stacked one atop the next, each sheet having a first side spaced apart from a third side, a second side spaced apart from a fourth side;
a releasable bond partially securing the fourth side of all sheets;
an interior circular border defining a interior of each sheet designated as a bulls eye;
a smaller circular center bulls eye within the bulls eye;
a surfactant foaming agent capsule within the bulls eye, whereby the capsule releases the foaming agent upon water contact.

10. The apparatus according to claim 9 wherein the foaming agent selected from the group consisting of:
sodium bicarbonate;
sodium lauryl sulfate;
ammonium lauryl sulfate.

11. The apparatus according to claim 10 wherein the foaming agent further comprises a dye.

* * * * *